United States Patent [19]

Myers

[11] Patent Number: 5,083,465

[45] Date of Patent: Jan. 28, 1992

[54] PROBE FOR AN EXTENSOMETER

[75] Inventor: Jeffrey L. Myers, West Chester, Ohio

[73] Assignee: General Electric Company, Cincinnati, Ohio

[21] Appl. No.: 632,799

[22] Filed: Dec. 24, 1990

[51] Int. Cl.⁵ .................................................. G01B 5/30
[52] U.S. Cl. ........................................ 73/826; 33/790
[58] Field of Search .................... 73/826, 837; 33/790, 33/788; 24/523

[56] References Cited

U.S. PATENT DOCUMENTS

| | | | |
|---|---|---|---|
| 608,012 | 7/1898 | Stirckler | 24/523 X |
| 3,319,338 | 5/1967 | DeNicola | 33/790 |

FOREIGN PATENT DOCUMENTS 2088065  6/1982  United Kingdom .................. 73/826

Primary Examiner—Jerry W. Myracle
Attorney, Agent, or Firm—Jerome C. Squillaro; Carmen Santa Maria

[57] ABSTRACT

Disclosed herein are probes for mounting on an extensometer used in conjunction with a materials testing machine, and can be used in high temperature applications. Each probe includes a probe shaft with a tip and a probe support body mounted to a hollow shield tube over the probe shaft. The probe support body includes a tipped segment which is biased toward the tip of the probe shaft. A longitudinal axis passes through the tips and tipped segment, respectively. The hollow shield tube mounted over the probe shaft is made of a high temperature material having a low thermal conductivity coefficient. The sleeve prevents excessive temperature transients from affecting the probe shaft.

27 Claims, 8 Drawing Sheets

PROBE FOR AN EXTENSOMETER

1. FIELD OF THE INVENTION

This invention relates generally to extensometers and, more particularly, to an improved attachment for a contact probe mounted to an extensometer for use in high temperature applications.

2. DESCRIPTION OF THE PRIOR ART

Generally, extensometers are instruments used for measuring minute deformations in materials acted upon by an external force. Several types of extensometers are disclosed in the following U.S. Pat. Nos.: 4,884,456; 3,600,939; 3,295,365 and 2,545,482. The measurements taken by extensometers typically pertain to deformation of the test specimen prior to its rupture. From this information, the yield stress, the modulus of elasticity and ultimate strain can be determined. This information is extremely important in the development and characterization of materials.

Typically, extensometers attach to a test specimen by application of force by spring-loading through the use of a leaf spring arrangement or by clamping. These clamps or probes may be either spring-mounted onto the specimen, such as that disclosed in U.S. Pat. Nos. 3,295,365 and 3,600,939, or threadably clamped onto the specimen, such as that disclosed in U.S. Pat. Nos. 4,251,918 and 4,884,456. Typically, these clamps or probes are bulky, difficult to handle or are complicated to manufacture. Further, the clamps and probes presently used induce undesirable bending stresses within the test specimen. The method of loading and the extent of loading also introduce undesirable stress concentrations into the specimen. These factors can affect the measured yield stress, ultimate strain and modulus of elasticity by weakening the test sample resulting in lower measured elongation values than had the bending stresses not been present. The problem is accentuated further in high temperature applications.

Therefore, it is an object of the invention to provide an extensometer probe which does not add bending stresses to the testing element. It is a further object of the invention to provide an extensometer probe which is inexpensive to manufacture and simple to operate.

A further problem experienced with known high temperature extensometers is caused by rapid heating of the test sample and the type of probes commonly used. Typically, the probes attach to the test sample at room temperature and then both the probes and test sample are subjected to accelerated heating rate and high elevated temperatures, for example, a test temperature of about 1500° C. and a heating rate of about 20.5° C. per minute. The part under test is held at this elevated temperature, while the extensometer, located a short distance away, typically about six inches, is at a much lower temperature, usually ambient temperature. As a result of the severe temperature gradient between the sample and the extensometer, radiant temperature transients and convective air currents result. These radiant and convective transfers cause temperature transients which affect dimensional changes in the probes during testing and cause erroneous extensometer measurements. Even small temperature transients result in changes in the dimensions of the extensometer probe which are amplified by the extensometer transducer, which results in erroneous measurements since the changes reflect dimensional changes in the probe rather than dimensional changes in the material under test.

Thus, it is desirable to provide an extensometer probe that reduces or eliminates errors in measurement associated with dimensional changes in the probe due to heat transients in high temperature applications.

SUMMARY OF THE INVENTION

Accordingly, I have invented a probe for attachment on an extensometer to measure the elongation of a test specimen along a first longitudinal axis passing through the test specimen. The probe includes an elongated probe shaft with a first end for mounting to the extensometer. The probe shaft has a second end having a tip. The probe shaft has a shoulder intermediate between the first end and the second tip end. The probe shaft shoulder may extend to the first end of the probe shaft and the extensometer may mount directly to this shoulder. A second longitudinal axis passes through the shaft from the first end through the tip end. The second longitudinal axis is transverse to the first longitudinal axis.

A hollow shield tube is mounted over the probe shaft and is radially spaced apart from the probe shaft. The shield tube has an outer diameter about the same size as the probe shaft shoulder and an inner diameter larger than the diameter of the probe shaft. The hollow shield tube is mounted opposite the first end of the probe shaft, having a first end which mates with the probe shaft shoulder and extends toward the probe shaft second end. The diametrical difference between the inner diameter of the hollow shield tube and the outer diameter of the probe shaft is essential to assure the probe shaft is spaced apart from the hollow shield tube.

A probe support body mounts to the hollow shield tube. The probe support body has a first apertured end, containing an aperture. The second end of the hollow shield tube is received by the aperture, which has a central axis corresponding to the second longitudinal axis of the probe shaft. The hollow shield tube may be secured to the probe support body within this aperture by any conventional means, such as, mechanical fastening means, adhesives, or, if appropriate, brazing or welding. The probe support body has a tipped segment end having a tipped portion oppositely disposed the apertured end and the aperture. The second end of the probe shaft, located in the hollow shield tube, extends through the aperture while remaining out of contact with the apertured end. The second longitudinal axis of the probe shaft is extended through the tipped portion of the tipped segment end of the probe support body. A plane extending through the first longitudinal axis of the test specimen and the second longitudinal axis of the probe shaft through the probe shaft tip end and extending through the support probe body tipped portion define a cross-section of the probe shaft tip end and the support probe body tipped portion. The tipped portion and tip end are oppositely disposed.

A biasing means, such as a spring, having an inner diameter slightly smaller than the outer diameter of the hollow shield tube and the shoulder of the probe shaft, is snugly fitted over both the hollow shield tube and the shoulder of the probe shaft. The snug fit permits the biasing means to exert a force on the tipped portion of the probe support body urging the tipped portion against the tip end of the probe shaft when the biasing means is in the relaxed or unextended position. When the biasing means is extended, the tipped portion is separated from the tip end of the probe shaft thereby causing a gap between the tipped portion and the probe shaft tip end so that a test specimen may be inserted therebetween. When the biasing means is then relaxed, a force is exerted on the tipped portion urging the tip portion against the test specimen transverse to the first longitudinal axis of the specimen. The specimen is further urged against the tip end of the probe shaft, thereby holding the specimen in position.

The probe shaft tip can be in the shape of a knife edge. Likewise, the tipped portion can be in the shape of a knife edge. The probe support body may include the hollow shield tube as an integral portion of the probe support body, rather than as two separate parts subsequently joined together. The biasing means may be a spring made of metal. The probe support body and hollow shield tube, may preferably be made of material having a low thermal conductivity such as ceramic.

The probe shaft is received by and is coaxial with the hollow shield tube and a first end of the tube is mounted to the probe shaft shoulder. The hollow shield material can be made of ceramic or metal, depending upon the temperature at which testing is performed. When the hollow shield material is a ceramic, it can include a material selected from the group of materials consisting of mullite, alumina, silicon carbide and graphite. Further, the annular gap defined between an inner surface of the hollow shield tube and an outer surface of the probe shaft maintains these parts in spaced relation and out of contact.

The support probe body 92 can include a first segment integrally attached to the first tipped segment and a recess for receiving the test specimen defined between the tipped segment and the first segment. An end of the hollow shield tube attaches to the first segment and the first probe shaft passes through the first segment and is contained within the recess.

The above-described probe is for mounting on an extensometer and can be incorporated in a testing machine or other measuring device, where first and second spaced apart probes are mounted to an extensometer. The testing machine also includes a body and a first grip and a second grip mounted to the body. The first grip and the second grip are adapted to hold and elongate the test specimen along a first longitudinal axis which passes through the test specimen. The testing machine also includes a device for moving the first grip and the second grip along the first axis and an extensometer mounted to the body.

To ensure that the above-described probes are properly spaced the measuring device can include a removable device for maintaining a fixed distance between the probes. This removable device can include a prong-receiving hole located in each of the probe support bodies and a spacing device having two prongs spaced a fixed distance apart where each of the prongs are slideably and removably received by a respective prong-receiving hole.

An advantage of the present invention is that the probe is shielded from temperature transients, thereby preventing these transients from affecting the probe, which in turn, affects the transducer. The measurement error heretofore associated with the temperature transients, referred to as thermally induced noise, and which currently must be filtered, factored into the measured results, or eliminated by modified extensometer design, is effectively eliminated by the present invention.

A further advantage of the present invention is that the mounting forces imposed on the test specimen are significantly lower than loadings imposed by prior art probes. The forces imposed by the probe of the present invention are imposed equally and oppositely across the face of the specimen. Thus, bending stresses are essentially eliminated and stress concentration factors are significantly reduced. This eliminates premature failure of the test specimen which is a serious problem with prior art probes.

Still another advantage of the present invention is the clip-on mounting feature, which provides for quick, accurate and repeatable mounting of the test specimens to the probe.

Finally, the probe of the present invention is low in cost and is readily adaptable to existing extensometer systems.

DESCRIPTION OF THE PREFERRED EMBODIMENTS

Figure 1:
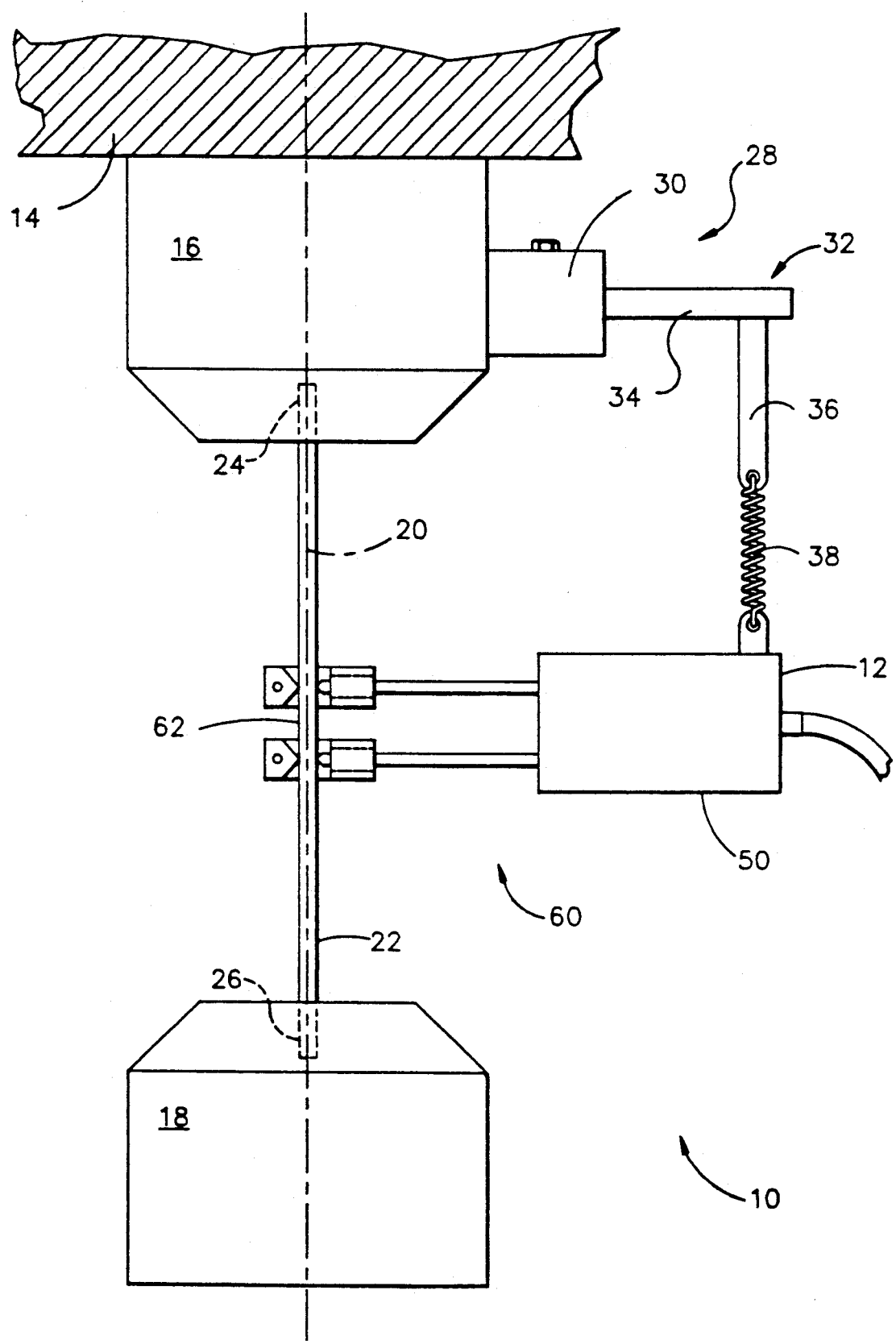
FIG. 1 is a side elevational view of a portion of a tensile testing machine including an extensometer having extensometer probes made in accordance with the present invention.

FIG. 1 shows a tensile testing assembly 10 having an extensometer 12. The tensile testing assembly 10 includes a body 14, a first grip 16 and a second grip 18. The first grip 16 and the second grip 18 are attached to the body 14 and spaced apart from each other along a longitudinal axis 20. The grips 16, 18 are adapted to move in opposite directions along the longitudinal axis 20. The grips 16, 18 hold a test specimen 22. Specifically, ends 24, 26 of the specimen 22 are held in place by grips 16, 18, respectively. A motor or a hydraulic drive mechanism (not shown) moves the grips 16, 18 in opposite directions along the longitudinal axis 20. The body/grip arrangement is well known in the art and is discussed in U.S. Pat. No. 4,884,456.

An extensometer holding assembly 28 attaches to the first grip 16. The grip 16 has an outer housing made of a magnetic attracting material, such as a ferrous material. A base 30 of the extensometer holding assembly 28 is magnetic and is magnetically held in place to the outer housing of the grip 16. A hanger assembly 32 depends outwardly from the base 30 and includes a first leg 34 having one end attached to the base 30 and a second end attached to one end of a second leg 36. A support spring 38 mounts to the other end of the second leg 36.

A water-cooled extensometer 50, which is well known in the art, also mounts to the spring 38. Although a strain-gaged bridge extensometer is disclosed herein, any type of extensometer that incorporates stand-off can be utilized. A probe assembly 60 attaches to the extensometer 50. The probe assembly 60 releasably attaches to a middle section 62 of the test sample 22.

Figure 2:
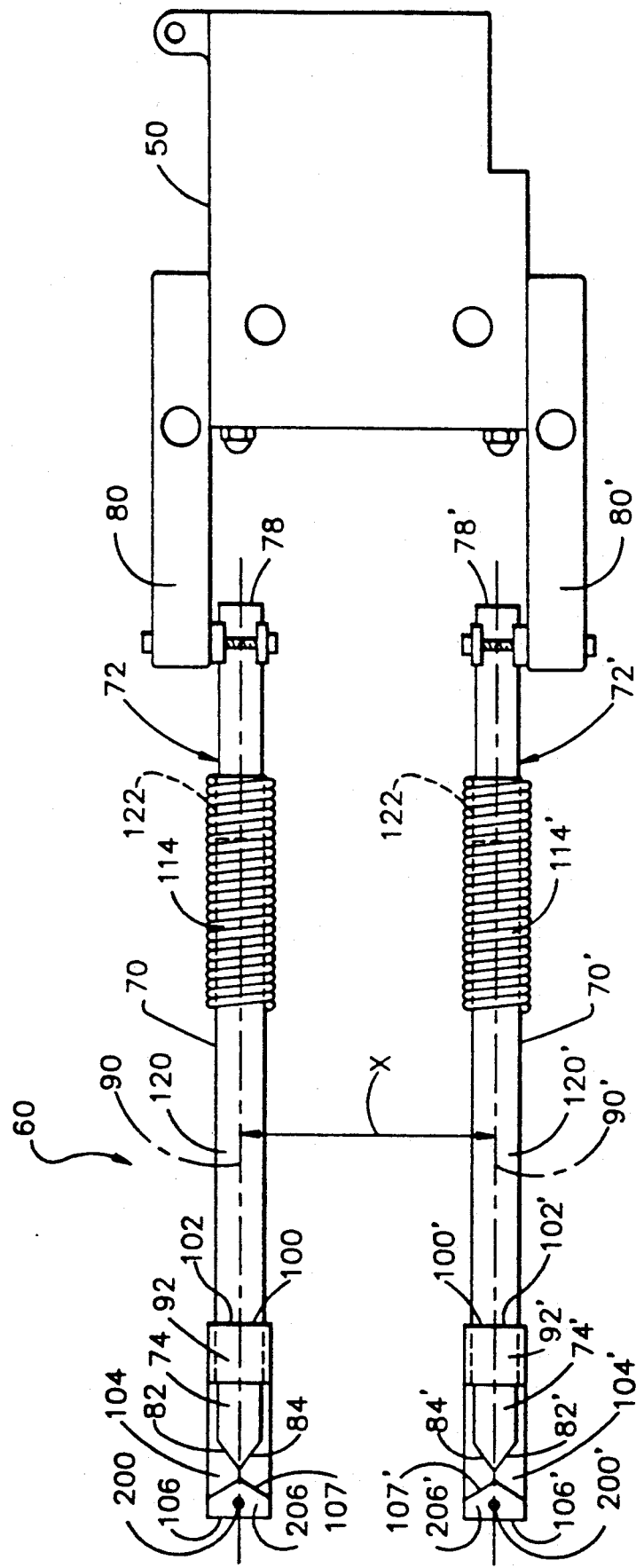
FIG. 2 is a side view of the extensometer and a first probe and a second probe made in accordance with the present invention.
Figure 3:
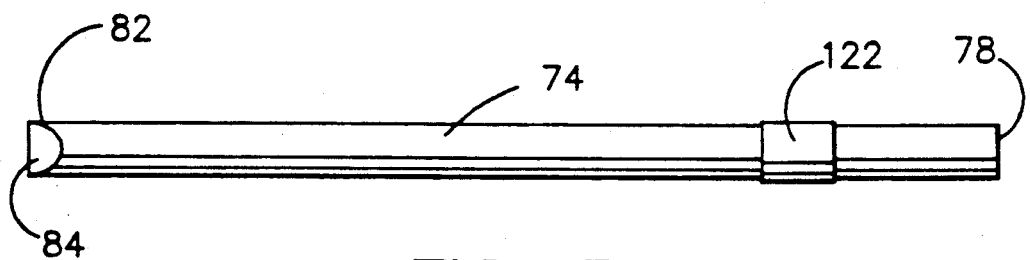
FIG. 3 is a top plan view of a probe shaft made in accordance with the present invention.
Figure 4:
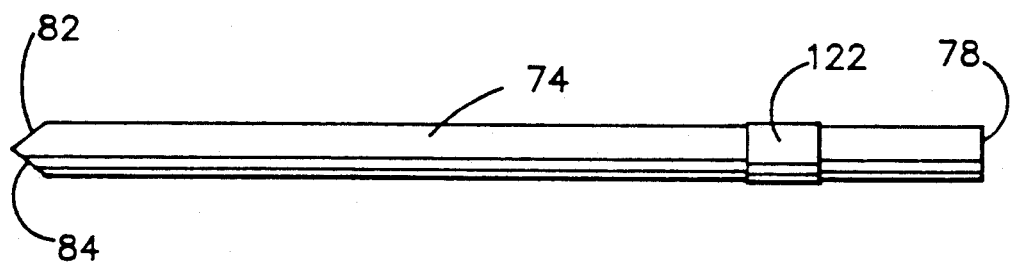
FIG. 4 is a side view of the probe shaft made in accordance with the present invention.
Figure 5:
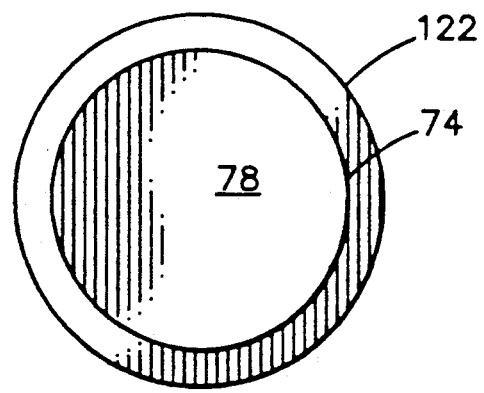
FIG. 5 is an end view of the probe shaft.

FIG. 2 shows the extensometer 50 and the probe assembly 60 in greater detail. The probe assembly 60 includes two probes 72 and 72' which are received by the extensometer 50. Probes 72 and 72' are similar to each other. Accordingly, like reference numerals will be used to describe like parts, where probe 72 reference numerals are primed. As shown in FIGS. 3-5, each probe 72, 72' includes a cylindrical probe shaft 74 having a first end 78 fastened to an extensometer arm 80 and as shown in FIGS. 2-3, a second end 82 having a probe tip 84 in the shape of a knife edge. The extensometer arm 80 also attach's to the extensometer 50. The probe 72 has a longitudinal axis 90 passing through the probe tip 84 located on the second end 82, and the first end 78 of the probe shaft 74. The axis 90 is substantially aligned perpendicular to the axis 20.

Figure 6:
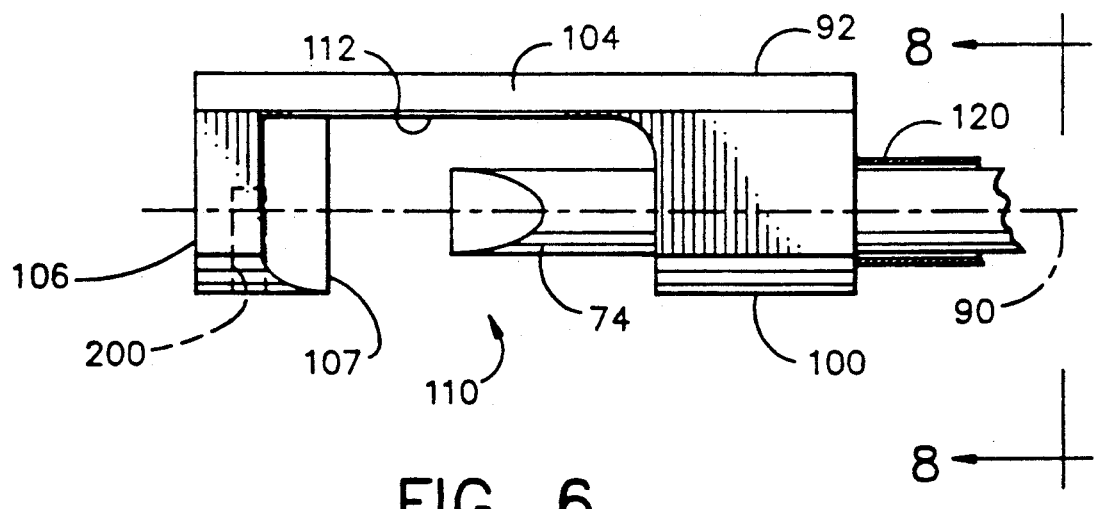
FIG. 6 is a top plan view of the support probe body.
Figure 7:
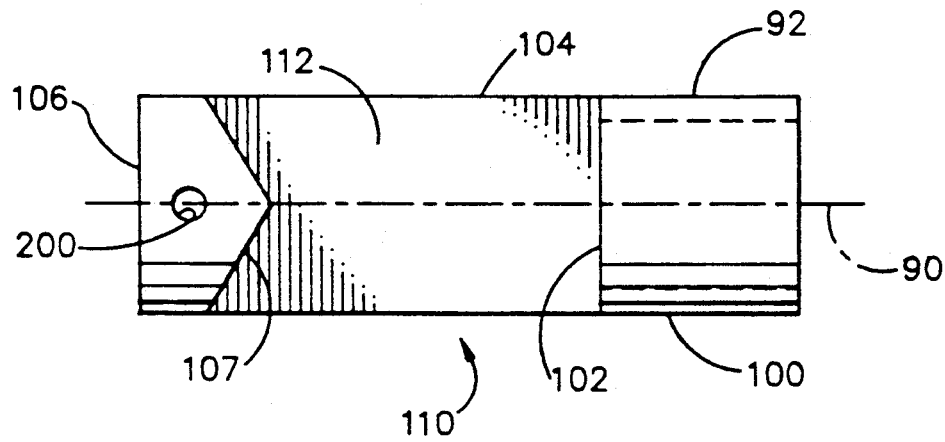
FIG. 7 is a side elevation of the support probe body of FIG. 6.
Figure 8:
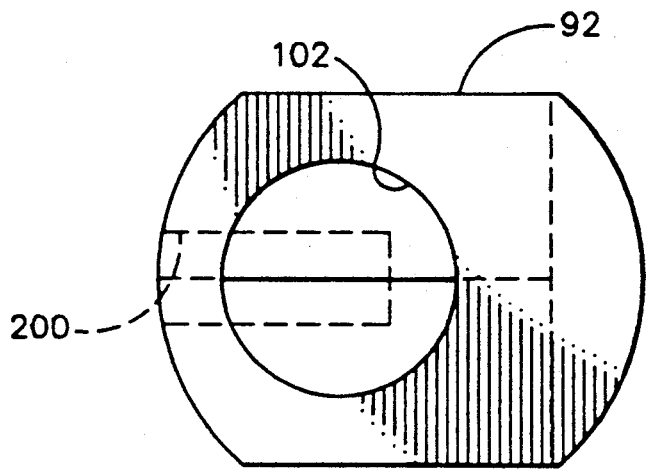
FIG. 8 is an end view of the support probe body of FIGS. 6-7.
Figure 9:
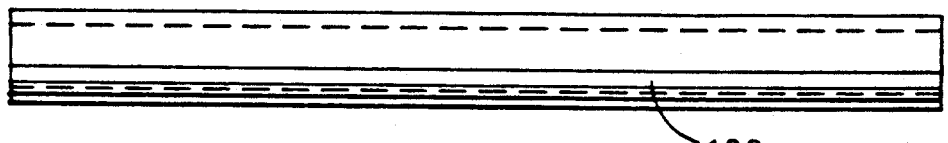
FIG. 9 is a side view of a shield tube made in accordance with the present invention.
Figure 10:
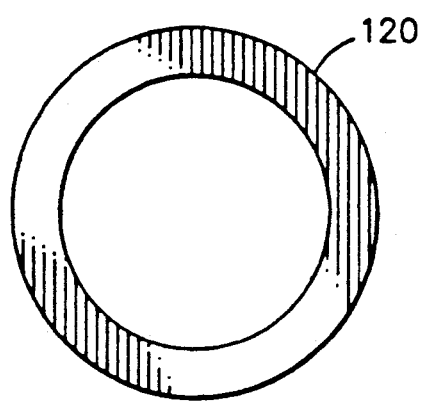
FIG. 10 is an end view of the shield tube.

Support probe body 92 fits or slips over the probe shaft 74. As shown in FIGS. 6-8, the support probe body 92 includes a rectangularly shaped apertured end 100 having an aperture 102 for receiving a shield tube 120 and probe shaft 74 passing therethrough, an integral middle segment 104 and an integral tipped segment 106. The tipped segment 106 includes a knife-edged tipped portion 107 oppositely disposed of the aperture 102. The axis 90 also passes through the central axis of the aperture 102 and the tipped portion 107. The inner surface 108 of the apertured end 100, a first surface 112 of middle segment 104 and the knife-edged tipped portion 107 define a sample receiving recess 110.

Referring to FIGS. 2-4 and 9-12, the support probe body 92 attaches to the probe shaft 74 by a spring-loaded arrangement that includes a cylindrical helical spring 114, a hollow shield tube 120 and a shoulder 122. Preferably, the spring 114 is made of metal. The tube 120 has a first end and second end, and is cylindrically shaped and is received by and coaxial with the probe shaft 74. The inner diameter of the tube 120 is greater than the outer diameter of the probe shaft 74, say on the order of 1/16". The length of the shield tube 120 is less than the length of the probe shaft 74. Preferably, the shield tube material 120 is a high temperature material having low thermal conductivity, such as mullite, alumina, silicon carbide or other ceramic material. The shield tube 120 can also be made of graphite. The second end of the shield tube 120 is received by aperture 102 of the support probe body 92 and is fixedly attached thereto by mechanical means or an adhesive. Alternatively, the shield tube 120 can be integrally formed with the support probe body 92. The first end of the shield tube 120 abuts against or contacts the shoulder 122. The shoulder 122 is a cylindrically shaped sleeve having an outer diameter or surface about the same diameter as the outer diameter of the shield tube 120 and is positioned between the first end 78 and the tip 84. The shoulder 122 is fixedly attached to the probe shaft 74 preferably, the shoulder 122 is affixed to the probe shaft with an alumina adhesive. The spring 114 has an internal diameter slightly less than the outer diameter of both the shield tube 120 and the shoulder 122, by about several thousandths of an inch. A portion of the shield tube 120 and the shoulder 122 passes through the center of the spring so that the spring 114 is coaxial thereto. Because of the difference of the spring inner diameter and the shield tube and shoulder outer diameter, the spring is attached to the shield tube 120 and shoulder 122 by a constrictive force for a snug fit. In this arrangement, the tip 84 is disposed through the aperture 102 and out of contact of the apertured end 100. The tip 84 is biased by spring 114 and urged toward the tipped portion 107.

Figure 12:
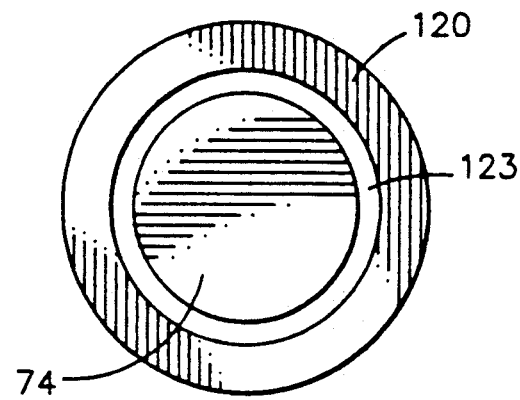
FIG. 12 is a cross-sectional view of the support probe shaft and the shield tube.
Figure 11:
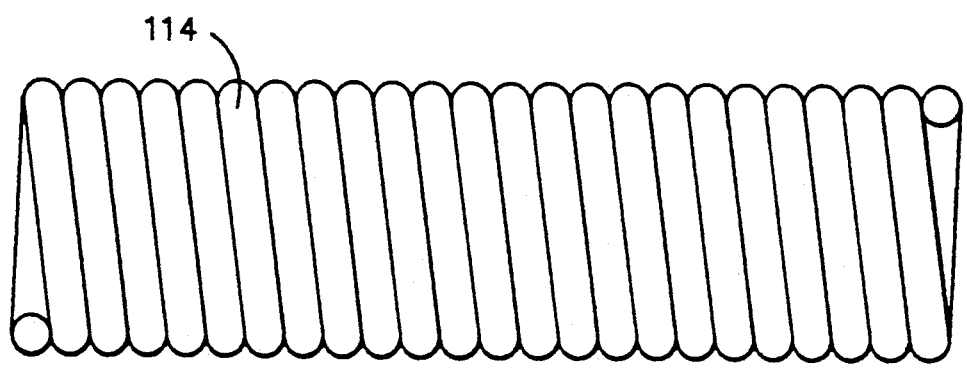
FIG. 11 is a side view of a spring used in the present invention.

As shown in FIG. 12, an annular gap 123 is defined between the inner surface of the shield tube 120 and the outer surface of the probe shaft 74. The gap 123 increases the thermal insulative properties of the shield tube 120 with respect to the probe shaft 74, especially in the case of convective currents.

Figure 13:
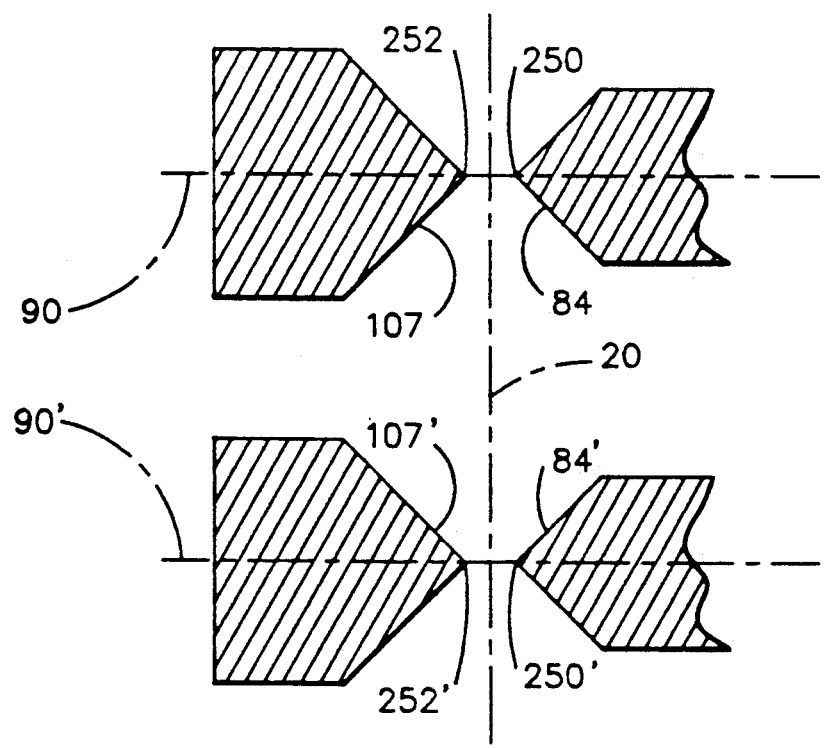
FIG. 13 is a partial cross-sectional view taken along a plane passing through the first probe and second probe.
Figure 14:
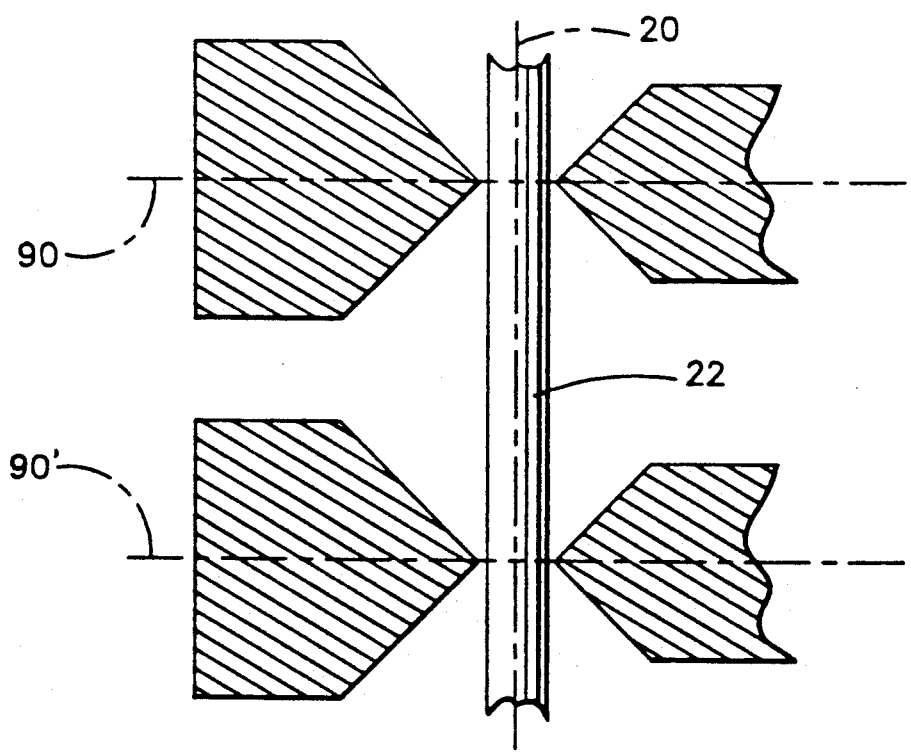
FIG. 14 is similar to FIG. 13 except the test specimen is positioned between the respective probe tips.
Figure 15:
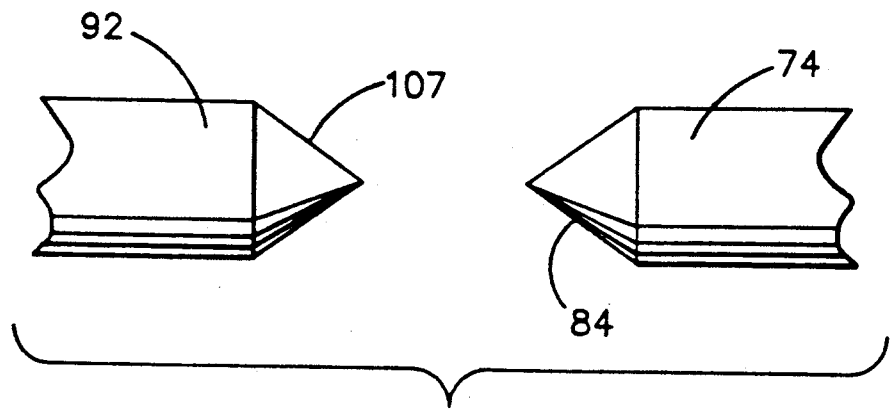
FIG. 15 shows a partial section of a probe having a conical tip and a conical tipped portion.
Figure 16:
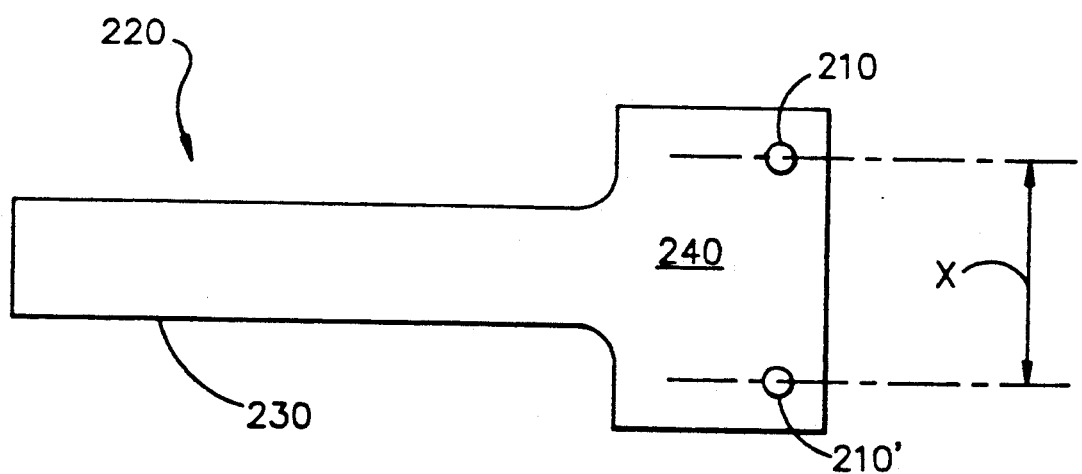
FIG. 16 shows a spacing device made in accordance with the present invention.

As can be seen by FIG. 2, probe 72' is positioned in spaced general parallel relation to the probe 72 a distance X along the longitudinal axis 20. A typical distance X may be ½"-2", but usually the distance is either ½" or 1". FIGS. 13 and 14 show a cross-sectional view of the tip 84 and tipped portion 107 of probe 72, and tip 84' and tipped portion 107' of the probe 72'. The cross-sectional view is caused by a plane passing through the probes 72, 72' and containing longitudinal axes 20, 90 and 90'. The cross-sections of the tip 84 and tipped portion 107, which are oppositely disposed, include apexes 250, 252, respectively and through which longitudinal axis 90 passes. Likewise, the cross-sections of the tip 84' and tipped portion 107' include apexes 250', 252', respectively, and through which longitudinal axis 90' passes. The sample specimen 22 is received between the apexes 250, 250' and 252, 252'. It should be noted that the tips 84, 84' and tipped portions 107, 107' need not be knife-edged shaped tut can be any shape having a cross-section with an apex, such as, for example, a parabolic cross-section. Further, the tips and tipped portions can be conical as shown in FIG. 15 or truncated cones.

In operation, tip portions 107, 107' are moved away from probe tips 84, 84' along axes 90, 90', respectively. The test specimen 22 is then received within recesses 110, 110'. Probe bodies 92, 92' are then released. The probes 72, 72' are frictionally held in place against the test specimen 22 by the tips 84, 84' and tipped portions 107 and 107' where the tipped portions 107, 107' and the tips 84, 84' are urged against the test specimen 22. Further, since the respective tips 84, 84' and tipped portions 107 and 107' are aligned along respective axes 90, 90', no bending moment is induced upon the test specimen 22. The environment adjacent to the probes 72, 72' and the test specimen 22 is then rapidly heated typically at a rate of 20.5° C./min., up to 1500° C. or more. Preferably, the shield tubes 120, 120' should not directly contact respective probe shafts 74, 74'. Otherwise, the shafts 74, 74' would act like thermal sinks to the shield tubes 120, 120' and would be affected by thermal transients.

It is important that the probes 72, 72' are properly spaced apart from each other. This is dependent upon the type of extensometer 50 used. Improperly spacing the probes 72, 72' will result in erroneous strain values of the test specimen 22.

To ensure that the probes 72, 72' are properly spaced apart, the probe support bodies are provided with holes 200, 200' on faces 206, 206' of the support probe body tipped segment 106, 106'. The holes 200, 200' are adapted to slideably receive cylindrical pins or prongs 210, 210' of a spacing device 220 shown in FIG. 15. The spacing device 220 further includes a handle 230 and a body 240 where the pins 210, 210' and the handle 230 attach to the body 240. The pins 210, 210' are spaced apart from each other the distance X, which is equal to the spacing of axis 90, 90'.

After the probes 72, 72' are attached to the test specimen 22, the pins 210, 210' are inserted into holes 200, 200', respectively. Then the pins 210, 210' are removed from the holes 200, 200'. This ensures that the probes 72, 72' are properly spaced apart from each other. The spacing device need not be limited to the pin and hole arrangement disclosed, for example, pins could extend from the tipped segments and the spacing device could have holes adapted to receive the pins or any other arrangement may be used to ensure the proper spacing of the probes.

Figure 17:
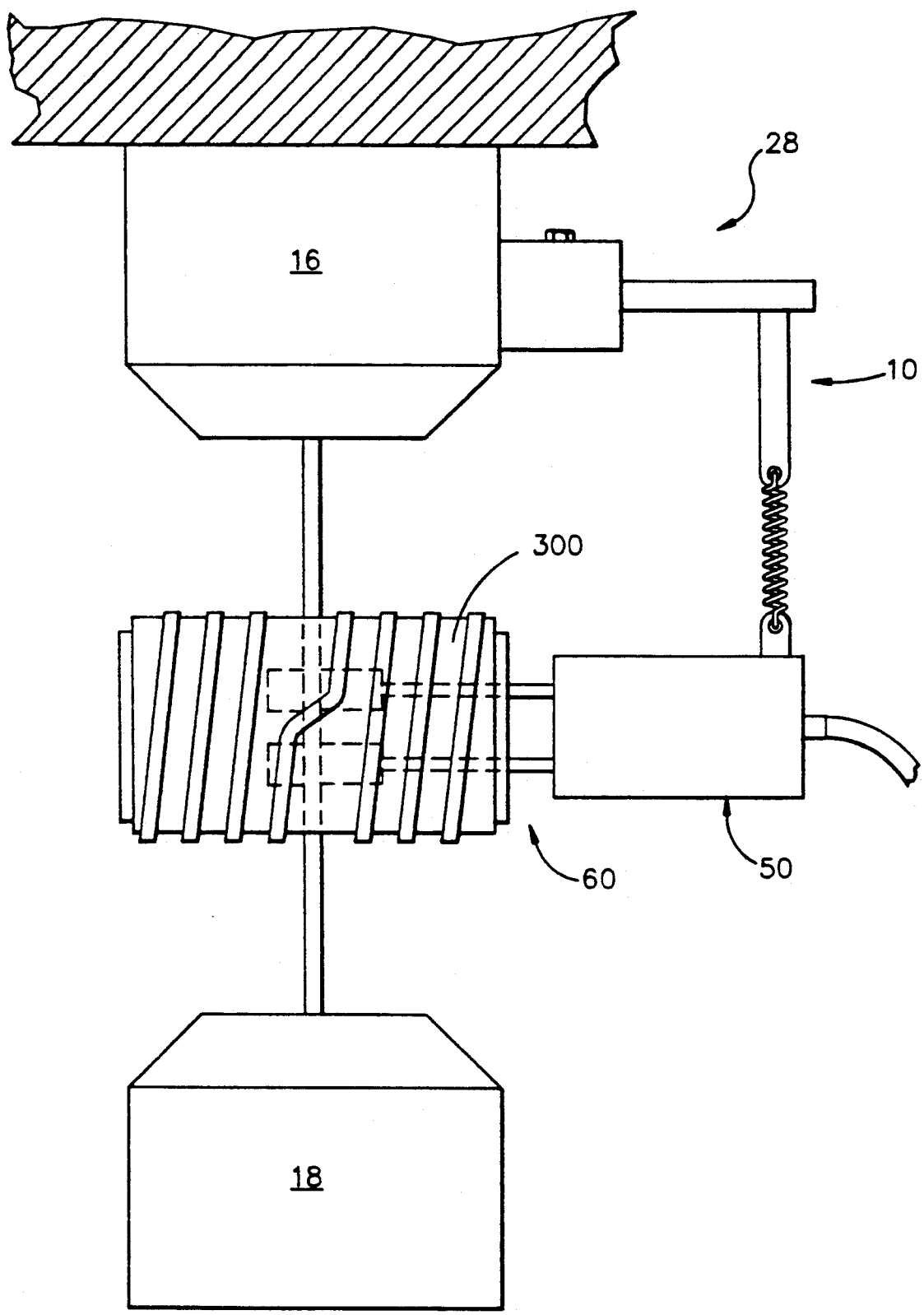
FIG. 17 is a schematic side elevational view of a tensile testing machine having a furnace positioned around the test specimen and the probes made in accordance with the present invention.

As shown in FIG. 17, a small furnace 300, which is well known in the art may be used. The grips 16, 18 are then moved away from one another along the axis 20. The deformation of the test specimen 22 along the longitudinal axis caused by thermal expansions and mechanical forces can be measured by the extensometer 50 in a manner well known in the art.

Probes made in accordance with those described herein eliminate induced bending stresses caused by prior art probes because the respective tips 107, 107', 92 and 92' are aligned along respective axes. Further, the coaxial action of the probes 72, 72' and shield tubes 120, 120' reduce the effects of thermally induced noise by shielding the probes from rapid and continuing temperature fluctuations resulting in more stable and accurate measurements of tensile properties. Furthermore, since few parts are required to manufacture the probes, manufacturing cost is less in comparison to many probes presently in use which are much more complicated in construction.

Having described the presently preferred embodiments of my invention, it is to be understood that it may otherwise be embodied within the scope of the appended claims.

What is claimed is:

1. A probe for attachment to an extensometer which measures deformation of a test specimen along a first longitudinal axis passing through the test specimen, comprising:
   (a) a probe shaft having a first end for mounting to the extensometer, a second end having a tip, a second longitudinal axis passing through said shaft from the first end through the second end, the second longitudinal axis transverse to the first longitudinal axis, and a shoulder between the first end and the second tip end;
   (b) a hollow shield tube having an outer diameter of about the same size as the probe shaft shoulder, said tube mounted over said probe shaft opposite said probe shaft first end and spaced apart from said probe shaft, said hollow shield tube having a first end in contact with the probe shaft shoulder and a second end;
   (c) a support probe body having an apertured end with an aperture having a central axis, the second longitudinal axis passing through the central axis of said aperture, for receiving the second end of said hollow shield tube, said probe shaft disposed through said aperture and out of contact with said apertured end,
   a tipped segment end having a tipped portion oppositely disposed said aperture, the second longitudinal axis extending through said tipped portion,
   the second longitudinal axis and a plane containing the first longitudinal axis defining the cross-section of said probe shaft tip end and said support probe body tipped segment end, wherein the cross-sections are oppositely disposed; and
   (d) a biasing means having an inner diameter and an outer diameter, said biasing means inner diameter being slightly smaller the outer diameter of said hollow shield tube and shoulder of said probe shaft, so that said biasing means fits snugly over siad hollow shield tube and said probe shaft shoulder, said biasing means urging said support probe body tipped segment end toward said tip end of said probe shaft, whereby when the test specimen is positioned between said support probe body tipped segment end and said tip end of said probe shaft, said support probe body tipped segment end is urged against the test specimen transverse to the first longitudinal axis, which is further urged against said probe shaft tip end.

2. The probe of claim 1 wherein said probe shaft tip end is in a shape of a knife edge.

3. The probe of claim 2 wherein said tipped portion of said support probe body tipped segment end is in a shape of a knife edge.

4. The probe of claim 1 wherein said hollow shield tube is an integral part of said support probe body.

5. The probe of claim 1 wherein said biasing means is a metallic spring.

6. The probe of claim 1 wherein said hollow shield tube is made of a material having a low thermal conductivity.

7. The probe of claim 6 wherein said hollow shield tube material is a ceramic.

8. The probe of claim 6 wherein said hollow shield tube material is selected from the group consisting of mullite, alumina, silicon carbide and graphite.

9. The probe of claim 6 wherein an annular gap is defined between an inner surface of said hollow shield tube and an outer surface of said probe shaft.

10. The probe of claim 9 wherein said support probe body further comprises a first segment integrally attached to said tipped segment end, a recess for receiving the test specimen being defined between said tipped portion of said tipped segment end and said first segment, and a second end of said hollow shield tube attaches to said first segment of said support probe body whereby said probe shaft passes through said first segment and said probe shaft tip end is contained within said recess.

11. The probe of claim 10 wherein said probe shaft tip end is a knife edge and said tipped portion of said tipped segment end of said support probe body is a knife edge.

12. A probe for mounting on an extensometer to measure the elongation of a test specimen along a first axis passing through the test specimen, comprising:
   (a) a probe shaft having a first end for mounting to the extensometer, and a second end having a tip;
   (b) a hollow shield tube having a first end mounted to said probe shaft, said hollow shield tube being coaxial with and spaced from at least a portion of said probe shaft, said hollow shield tube having an inner diameter larger than an outer diameter of said probe shaft portion, and said hollow shield tube having a second end; and
   (c) a support probe body mounted to said second end of said hollow shield tube, said support probe body having a tipped segment end oppositely disposed said probe shaft tip end whereby the test specimen is received between said support probe body tipped segment end and said probe shaft tip end.

13. The probe for mounting to an extensometer of claim 12 wherein said hollow shield tube is made of a material having a low thermal conductivity.

14. The probe for mounting on an extensometer of claim 13 wherein said hollow shield tube is a ceramic material.

15. The probe for mounting on an extensometer of claim 13 wherein said hollow shield tube is made of a material selected from the group consisting of mullite, alumina, silicon carbide and graphite.

16. The probe for mounting on an extensometer of claim 13 further comprising a shoulder attached to said probe shaft, and a spring having a first end mounted to said shoulder and a second end mounted to said first end of said hollow shield tube, and said second end of said hollow shield tube mounted to said support probe body whereby said spring biases said support probe body tipped segment end towards said probe shaft tip end.

17. The probe for mounting on an extensometer of claim 12 wherein an annular gap is defined between an inner surface of said hollow shield tube and an outer surface of said probe shaft portion.

18. A device to measure the elongation of a test specimen along a first longitudinal axis passing through the test specimen, comprising:
   an extensometer; and
   first and second spaced apart probes for mounted to the extensometer wherein each of said probes includes:
   (a) a probe shaft having a first end for mounting to the extensometer, a second end having a tip, a second longitudinal axis passing through said shaft from the first end through the second end, the second longitudinal axis transverse to the first longitudinal axis, and a shoulder between the first end and the second tip end;
   (b) a hollow shield tube having an outer surface of about the same size as the probe shaft shoulder, said tube mounted over said probe shaft opposite said probe shaft first end and spaced apart from said probe shaft, said hollow tube having a first end in contact with the probe shaft shoulder and a second end;
   (c) a support probe body having an apertured end with an aperture, the second longitudinal axis passing through the central axis of the aperture, for receiving the second end of said hollow shield tube, said probe shaft disposed through said aperture and out of contact with the apertured end, a tipped segment end having a tipped portion oppositely disposed said aperture, the second longitudinal axis extending through the tipped portion, the second longitudinal axis and a plane containing the first longitudinal axis defining the cross-sections of the probe shaft tip end and the support probe body tipped portion, wherein the cross-sections are oppositely disposed; and
   (d) a biasing means having an inner diameter and an outer diameter, the inner diameter being slightly smaller than the outer diameter of said hollow shield tube and the shoulder of said probe shaft, so that said biasing means fits snugly over said hollow shield tube and the shoulder of said probe shaft, said biasing means urging the tipped portion of said portion probe body toward said tip end of said probe shaft whereby when the test specimen is positioned between the tipped portion of said support probe body and said tip end of said probe shaft, said tipped portion is urged against the test specimen transverse to the first longitudinal axis, which is further urged against the tip end of said probe shaft.

19. The device of claim 18 wherein the biasing means of each probe is a spring made of metal.

20. The device of claim 18 wherein said hollow tube of each probe is made of a material having a low thermal conductivity.

21. The device of claim 20 wherein said material having a low thermal conductivity is a ceramic material.

22. The device of claim 18 further comprising removable means for maintaining a fixed distance between said probes.

23. The device of claim 22 wherein said removable means comprises a prong-receiving hole located in each of said support probe bodies and a spacing device having two prongs spaced a fixed distance apart, each of said prongs slideably and removably received by a respective prong-receiving hole.

24. A device to measure the elongation of a test specimen along a first longitudinal axis passing through the test specimen, comprising:
   an extensometer; and
   first and second spaced apart probes for mounting to the extensometer wherein each of said probes includes:
   (a) a probe shaft having a first end for mounting to the extensometer and a second end having a tip;
   (b) a hollow shield tube made of a material having a low thermal conductivity and having an inner diameter and an outer diameter, at least a portion of said probe shaft received within and spaced from said inner diameter and coaxial with said hollow shield tube, and said hollow shield tube further having a first end mounted to said probe shaft; and
   (c) a support probe body mounted to said probe shaft, said support probe body having a first tipped segment end oppositely disposed said probe shaft tip end, wherein said probe receives the test specimen between said support probe body tipped segment end and said probe shaft tip end.

25. The probe for mounting on an extensometer of claim 24 further comprising a spring having one end mounted to said probe shaft and the other end mounted to said first end of said hollow shield tube, and a second end of said hollow shield tube mounted to said support probe body whereby said support probe body tipped segment end is biased toward said probe shaft tip end.

26. The device of claim 25 further comprising removable means for maintaining a fixed distance between said probes.

27. A materials testing machine comprising:
a body;
a first grip and a second grip mounted to said body, said first grip and said second grip adapted to hold and elongate a test specimen along a first longitudinal axis which passes through the test specimen;
means for moving said first grip and said second grip along the first axis;
an extensometer mounted to said body; and
and spaced apart probes for
first and second spaced apart probes for mounting to said extensometer, wherein each probe includes:
(a) a probe shaft having a first end for mounting to the extensometer, a second end having a tip, a second longitudinal axis passing through said shaft from the first end through the second end, the second longitudinal axis transverse to the first longitudinal axis, and a shoulder between the first end and the second tip end;
(b) a hollow shield tube having an outer surface of about the same size as the probe shaft shoulder, said tube mounted over said probe shaft opposite said probe shaft first end and spaced apart from said probe shaft, said hollow tube having a first end in contact with the probe shaft shoulder and a second end;
(c) a support probe body having an apertured end with an aperture, the second longitudinal axis passing through the central axis of the aperture, for receiving the second end of said hollow shield tube, said probe shaft disposed through said aperture and out of contact with the apertured end,
a tipped segment end having a tipped portion oppositely disposed said aperture, the second longitudinal axis extending through the tipped portion,
the second longitudinal axis and a plane containing the first longitudinal axis defining the cross-sections of the probe shaft tip end and the support probe body tipped portion, wherein the cross-sections are oppositely disposed; and
(d) a biasing means having an inner diameter and an outer diameter, the inner diameter being slightly smaller than the outer diameter of said hollow shield tube and the shoulder of said probe shaft, so that said biasing means fits snugly over said hollow shield tube and the shoulder of said probe shaft, said biasing means urging the tipped portion of said support probe body toward said tip end of said probe shaft whereby when the test specimen is positioned between the tipped portion of said support probe body and said tip end of said probe shaft, said tipped portion is urged against the test specimen transverse to the first longitudinal axis, which is further urged against the tip end of said probe shaft.

* * * * *